(12) United States Patent
Lee et al.

(10) Patent No.: US 10,061,901 B2
(45) Date of Patent: Aug. 28, 2018

(54) PREDICTION METHOD FOR MIXED SOLVENT FOR MINIMIZING AMOUNT OF SINGLE SOLVENT USED, AND SYSTEM USING SAME

(71) Applicant: LG CHEM, LTD., Seoul (KR)

(72) Inventors: Seungyup Lee, Daejeon (KR); Hyesung Cho, Daejeon (KR); Changik Song, Daejeon (KR)

(73) Assignee: LG CHEM, LTD., Seoul (KR)

(*) Notice: Subject to any disclaimer, the term of this patent is extended or adjusted under 35 U.S.C. 154(b) by 470 days.

(21) Appl. No.: 14/434,336

(22) PCT Filed: Jul. 11, 2014

(86) PCT No.: PCT/KR2014/006234
§ 371 (c)(1),
(2) Date: Apr. 8, 2015

(87) PCT Pub. No.: WO2015/008976
PCT Pub. Date: Jan. 22, 2015

(65) Prior Publication Data
US 2015/0294091 A1    Oct. 15, 2015

(30) Foreign Application Priority Data

Jul. 17, 2013 (KR) .................... 10-2013-0084080

(51) Int. Cl.
*G06F 17/10* (2006.01)
*G06F 19/00* (2018.01)

(52) U.S. Cl.
CPC ............ *G06F 19/704* (2013.01); *G06F 17/10* (2013.01); *G06F 19/70* (2013.01)

(58) Field of Classification Search
CPC ...................................................... G06F 19/704
USPC ............................................................. 703/2
See application file for complete search history.

(56) References Cited

U.S. PATENT DOCUMENTS 6,238,679 B1   5/2001   de la Poterie
2007/0224551 A1  9/2007   Chou et al.

FOREIGN PATENT DOCUMENTS

| JP | 01-503237 A | 11/1989 |
| KR | 10-2010-0021100 A | 2/2010 |
| WO | 02/36669 A2 | 5/2002 |

OTHER PUBLICATIONS

Elidrissi, A., et al., "New approach to predict the solubility of polymers Application: Cellulose Acetate at various DS prepared from Alfa "Stipa-tenassicima" of Eastern Morocco", J. Mater. Environ. Sci., 3 (2) (2012) 270-285.
Abbott, Steven, et al., "Hansen Solubility Parameters in Practice Complete with software, data and examples", 3rd Edition, version 3.1, 2008-2010.

(Continued)

*Primary Examiner* — Hugh Jones
(74) *Attorney, Agent, or Firm* — Dentons US LLP

(57) ABSTRACT

The present invention relates to a prediction method for a mixed solvent for minimizing the amount of single solvents used, and to a system using same, and more specifically to a novel evaluation method that can predict a mixed solvent that minimizes the amount of single solvents used by using a graph-based mixing ratio dependent solubility estimation (G-MRDSE) that can calculate the maximum composition of additional solvents in a mixed solvent, and a system using same.

7 Claims, 8 Drawing Sheets

(56) References Cited

OTHER PUBLICATIONS

Hansen et al., "Hansen Solubility Parameters: A User's Handbook," Chapter 1 (Solubility Parameters—An Introduction), CRC Press LLC (2000) (24 pages).
"Hansen solubility parameter user forum," https://www.pirika.com/NewHP-J/JP/polymer-solvent.html, Sep. 9, 2009 (9 pages).
"Hansen solubility parameter user forum," https://www.pirika.com/NewHP-J/JP2/GreenSolvent.html, Jul. 28, 2010 (4 pages).

Solubility difference between polymer A and
mixed solvent B-D becomes small or similar
when D amount is increased to certain value
(critical value)

Solubility difference between polymer A
and mixed solvent B-D becomes large
when D amount exceeds critical value Polymer A Similar solubility
parameter: polymer A
is dissolved well in
single
solvent B Mixed solvent B+D ⬌ Single solvent B Solubility difference between single solvent B and
mixed solvent B-D becomes large as D amount
increases

FIG.6

PREDICTION METHOD FOR MIXED SOLVENT FOR MINIMIZING AMOUNT OF SINGLE SOLVENT USED, AND SYSTEM USING SAME

This application is a National Stage Entry of International Application No. PCT/KR2014/006234 filed Jul. 11, 2014, which claims priority to and benefit of Korean Application No. 10-2013-0084080 filed Jul. 17, 2013, in the Korean Intellectual Property Office, both of which are incorporated herein by reference.

TECHNICAL FIELD

The present invention relates to a prediction method for a mixed solvent for minimizing the amount of single solvents used, and to a system using same, and more specifically to a novel evaluation method that can predict a mixed solvent that minimizes the amount of single solvents used by using a graph-based mixing ratio dependent solubility estimation (G-MRDSE) that can calculate the maximum composition of additional solvents in a mixed solvent, and a system using same. This application claims the benefit of Korean Patent Application No. KR 10-2013-0084080, filed Jul. 17, 2013, which is hereby incorporated by reference in its entirety into this application.

BACKGROUND ART

A mixed solvent, obtained by mixing a single solvent for dissolving a specific substance with another kind of additional solvent, is changed in solubility characteristics compared to a single solvent. Furthermore, as the amount of the additional solvent increases, solubility of the mixed solvent becomes significantly different from that of the single solvent. Since a mixed solvent having solubility different from a single solvent is also different in solubility from a substance to be dissolved, for example, a polymer, it is typically regarded as impossible to be used for dissolving a polymer, instead of a single solvent.

Requirements for using a mixed solvent instead of a single solvent for dissolving a polymer are as follows: (1) a mixed solvent should have solubility similar to that of a single solvent so as to dissolve a polymer, and (2) a mixed solvent should contain an additional solvent in a maximum amount so that the amount of a single solvent is minimized. However, as the amount of the additional solvent is larger, a solubility difference between the mixed solvent and the single solvent may increase, and requirements (1) and (2) may not be simultaneously satisfied.

Meanwhile, in order to determine solubility or miscibility of substances, similarity of the substances should be compared using unique properties thereof. Among a variety of unique properties that affect solubility or miscibility, particularly useful is a solubility parameter for quantifying the extent of interaction of substances. Specifically, individual substances have unique solubility parameters, and substances having similar solubility parameters are dissolved in or are miscible with each other.

Among solubility parameters proposed and utilized based on various theories or concepts, the Hansen solubility parameter (HSP) devised by Dr. C. Hansen, 1967, is known to evaluate solubility characteristics very accurately. As for HSP, the extent of interaction of substances is considered by the following three elements:

(1) $\delta D$ is a nonpolar solubility parameter owing to dispersion interactions;

(2) $\delta P$ is a polar solubility parameter owing to permanent dipole-permanent dipole interactions; and (3) $\delta H$ is a hydrogen bond solubility parameter.

Thus, HSP is widely utilized to more accurately and systematically evaluate solubility or miscibility of the substances because it provides specific interaction information of the substances, compared to the other solubility parameters.

$$\text{HSP}=(\delta D, \delta P, \delta H), (\text{J/cm}^3)^{1/2} \tag{1}$$

$$\delta \text{Tot}=(\delta D^2+\delta P^2+\delta H^2)^{1/2}, (\text{J/cm}^3)^{1/2} \tag{2}$$

HSP is regarded as a vector having a magnitude and direction in a space made up of three elements, and $\delta$Tot shows the magnitude of HSP vector. A basic unit of the HSP is $(\text{J/cm}^3)^{1/2}$. Such HSP values are calculated using a program referred to as HSPiP (Hansen Solubility Parameters in Practice) by a research group led by Dr. Hansen, who developed HSP. As mentioned above, when two substances have similar HSP values, they dissolve well in each other. In order to determine that substances are similar, three HSP elements and the HSP magnitude of individual substances should be similar because HSP is a vector. All the substances are compared and analyzed for the similarity difference based on unique HSPs thereof, and thereby whether substances of interest may be dissolved in each other may be estimated.

Although whether pure substances are dissolved well in each other may be estimated via HSP similarity analysis of individual pure substances, a mixture comprising two or more kinds of pure substances may greatly vary in solubility depending on the composition thereof. The mixed solvent may be efficiently employed so as to be adapted for various purposes so long as solubility properties thereof are appropriately utilized. In particular, such a mixed solvent may play a great role in replacing a conventionally used single solvent or adjusting specific properties. For example, as shown in the flowchart of FIG. 1, when a great cost saving effect may be created under the condition that an expensive single solvent having high polymer solubility for use in polymer processing is replaced with another inexpensive single solvent, a desired purpose may be achieved in the presence of a replaceable single solvent, but solutions for cost savings have not yet been proposed in the absence of such a replaceable solvent.

Even if there is not provided a single solvent able to completely replace a conventional single solvent, cost savings may be ensured so long as the amount of a single solvent is maximally reduced, and thus solutions therefor are required.

Since the mixed solvent significantly varies in solubility characteristics depending on the composition thereof as mentioned above, the use of a mixed solvent may be considered as an alternative to reducing the amount of a single solvent. Although a variety of mixed solvents may be prepared depending on the kind of solvent used, the use of a mixed solvent made by adding another additional solvent that is inexpensive compared to a conventional single solvent may be taken into consideration.

Conditions necessary for using a mixed solvent in lieu of a single solvent are that a mixed solvent should have solubility similar to that of a single solvent so as to dissolve a target substance without particular problems and also that a mixed solvent should contain a single solvent in a minimum amount so as to maximize cost saving effects. However, the mixed solvent obtained by mixing a single solvent with another additional solvent is problematic because the solubility thereof varies. Therefore, there is a need to study a method of searching for a mixed solvent composition having solubility similar to that of a single solvent while maximally reducing the amount of a single solvent by properly adjusting the solubility of the mixed solvent.

DISCLOSURE

Technical Problem

The present invention has been made keeping in mind the above problems in the related art, and an object of the present invention is to provide a novel method of estimating a mixed solvent for minimizing the amount of a single solvent.

Technical Solution

In order to accomplish the above object, the present invention provides a method of estimating a mixed solvent for minimizing the amount of a single solvent, wherein in a target substance to be dissolved, a single solvent for dissolving the target substance, and a mixed solvent comprising the single solvent and an additional solvent, the mixed solvent that is used to dissolve the target substance contains the single solvent in a minimum amount, the method comprising:

a) calculating HSP of a mixed solvent prepared by adding a single solvent with an additional solvent, depending on an increase in wt % of the additional solvent of the mixed solvent;

b) calculating an HSP difference (HSP-Diff) between HSP of the mixed solvent calculated in a) and HSP of the target substance to be dissolved in the single solvent;

c) forming a two-dimensional graph of HSP-Diff depending on an increase in wt % of the additional solvent of the mixed solvent; and d) determining a maximum value (MAX) of wt % of the additional solvent such that HSP-Diff depending on the increase in wt % of the additional solvent of the mixed solvent is uniformly maintained within a deviation of 20% or less relative to HSP-Diff at 0 wt % of the additional solvent in the graph formed in c).

In addition, the present invention provides a system for estimating a mixed solvent for minimizing the amount of a single solvent, comprising:

a first data input module for receiving data for HSP of a mixed solvent prepared by adding a single solvent with an additional solvent depending on an increase in wt % of the additional solvent of the mixed solvent;

a second data input module for receiving data for HSP-Diff between HSP of the mixed solvent input to the first data input module and HSP of a target substance to be dissolved in the single solvent;

a graph determination module for forming a two-dimensional graph of HSP-Diff depending on an increase in wt % of the additional solvent of the mixed solvent; and a maximum value determination module for calculating a maximum value of wt % of the additional solvent such that HSP-Diff depending on the increase in wt % of the additional solvent of the mixed solvent is uniformly maintained within a deviation of 20% or less relative to HSP-Diff at 0 wt % of the additional solvent in the graph formed in the graph determination module.

Advantageous Effects

According to the present invention, a method of estimating a mixed solvent for minimizing the amount of a single solvent, namely, G-MRDSE is applied, and thereby solubility characteristics of substances are compared using HSP and a graph of calculated data results is analyzed, thus estimating the composition of a mixed solvent containing a single solvent in a minimum amount, ultimately ensuring price competitiveness. Furthermore, the present invention can be expected to be efficiently utilized in various fields due to the new approach to solubility estimation using HSP.

DESCRIPTION OF DRAWINGS

FIG. 6 is a schematic view illustrating a reduction or similarity in a solubility difference of a mixed solvent B+D prepared by adding a single solvent B with an additional solvent D when the amount of the additional solvent is increased to a critical value in Example 2 according to the present invention;

BEST MODE

Figure 1:
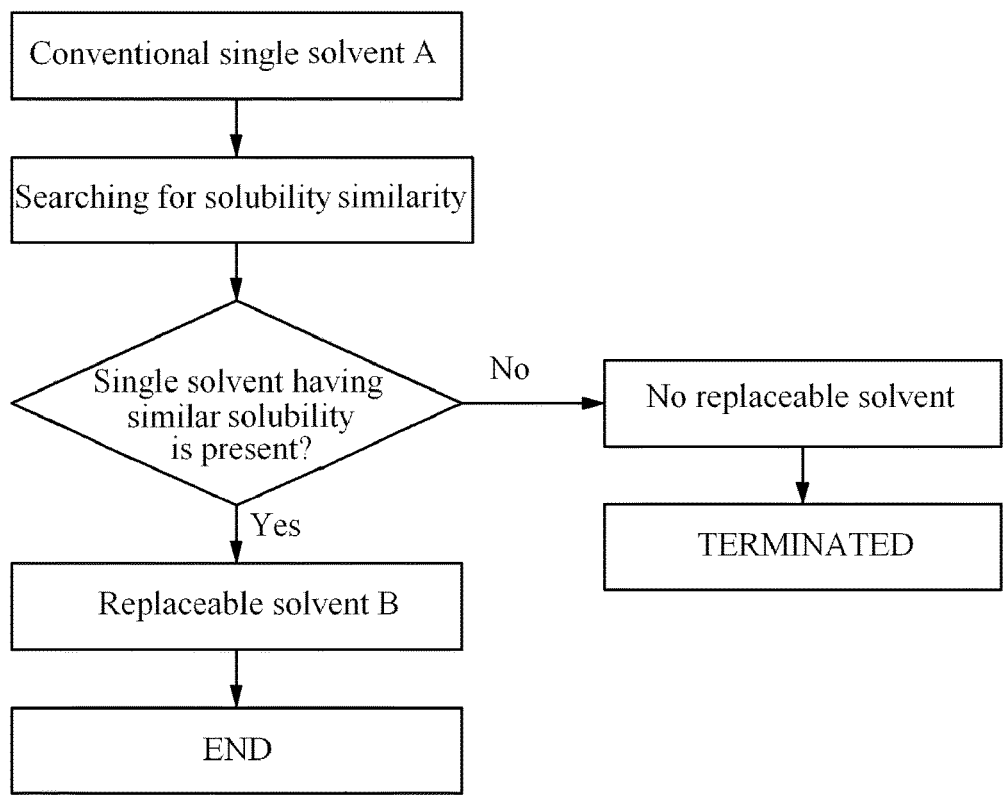
FIG. 1 is a flowchart illustrating a conventional process of searching for a replaceable solvent having solubility similar to that of a single solvent.
Figure 2:
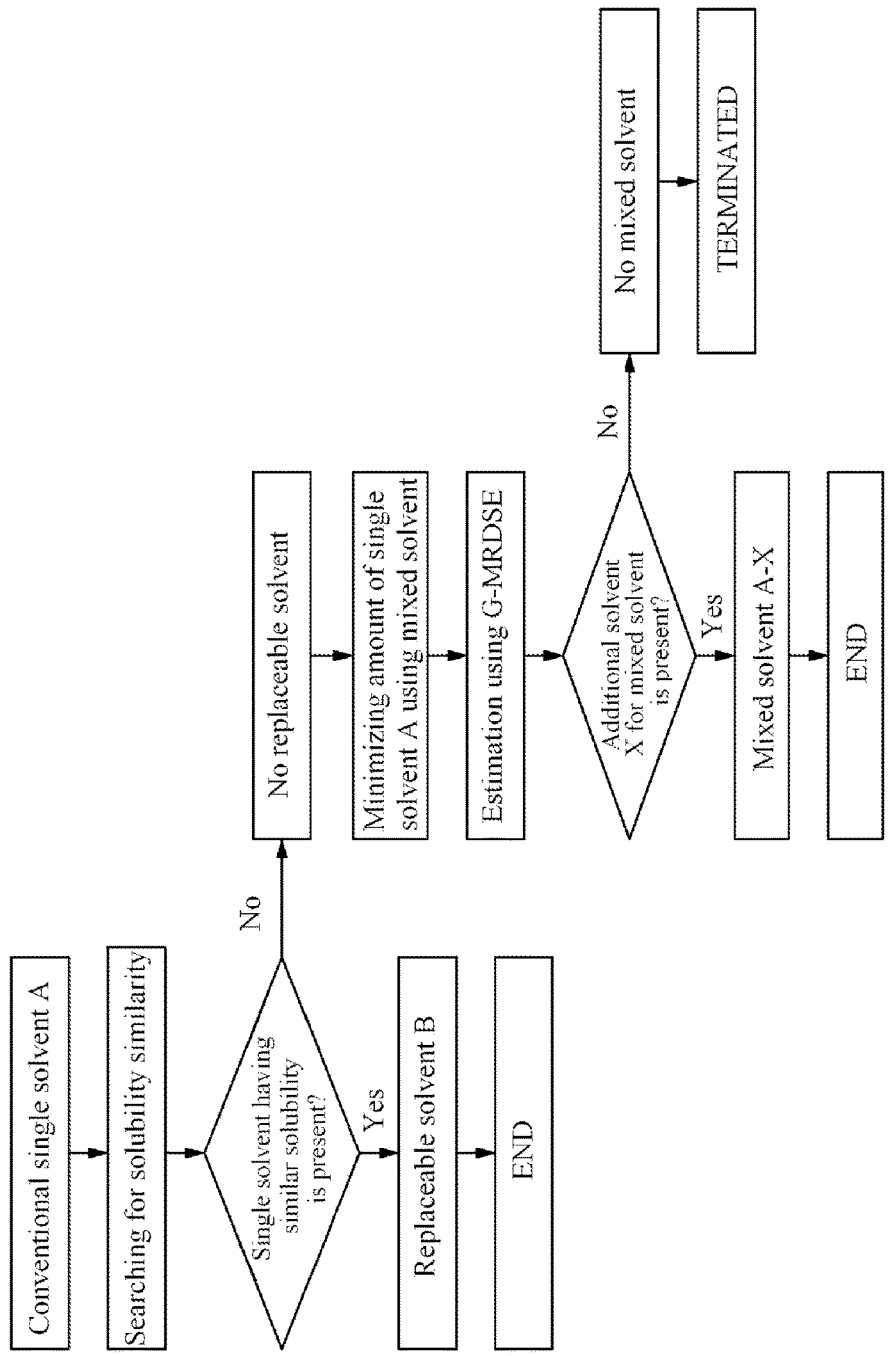
FIG. 2 is a flowchart illustrating a process of searching for a mixed solvent composition using G-MRDSE according to the present invention.

Hereinafter, a detailed description will be given of the present invention.

The present invention addresses a method of estimating a mixed solvent for minimizing the amount of a single solvent, wherein in a target substance to be dissolved, a single solvent for dissolving the target substance, and a mixed solvent comprising the single solvent and an additional solvent, the mixed solvent that is used to dissolve the target substance contains the single solvent in a minimum amount. The method comprises:

a) calculating HSP of a mixed solvent prepared by adding a single solvent with an additional solvent, depending on an increase in wt % of the additional solvent of the mixed solvent;

b) calculating HSP-Diff between HSP of the mixed solvent calculated in a) and HSP of the target substance to be dissolved in the single solvent;

c) forming a two-dimensional graph of HSP-Diff depending on an increase in wt % of the additional solvent of the mixed solvent; and d) determining a maximum value (MAX) of wt % of the additional solvent such that HSP-Diff depending on the increase in wt % of the additional solvent of the mixed solvent is uniformly maintained within a deviation of 20% or less relative to HSP-Diff at 0 wt % of the additional solvent in the graph formed in c).

By the present inventors, a method of estimating a mixed solvent for minimizing the amount of a single solvent is referred to as "G-MRDSE (Graph-based Mixing Ratio Dependant Solubility Estimation)".

In a), HSP of a mixed solvent obtained by adding a single solvent with an additional solvent is calculated depending on an increase in wt % of the additional solvent of the mixed solvent.

HSP is a vector having a magnitude and direction in a space made up of three elements, and $\delta$Tot shows the magnitude of HSP vector. A basic unit of the HSP is $(J/cm^3)^{1/2}$. Such HSP values are calculated using a program referred to as HSPiP (Hansen Solubility Parameters in Practice) by a research group led by Dr. Hansen, who developed HSP.

HSP is defined as HSP=($\delta$D, $\delta$P, $\delta$H) and $\delta$Tot as below.

$$HSP=(\delta D, \delta P, \delta H), (J/cm^3)^{1/2} \quad (1)$$

$$\delta Tot=(\delta D^2+\delta P^2+\delta H^2)^{1/2}, (J/cm^3)^{1/2} \quad (2)$$

As for HSP, the extent of interaction of substances is divided into the following three elements:

(1) $\delta$D is a nonpolar solubility parameter owing to dispersion interactions;

(2) $\delta$P is a polar solubility parameter owing to permanent dipole-permanent dipole interactions; and (3) $\delta$H is a hydrogen bond solubility parameter.

HSP is very useful for more accurately and systematically evaluating solubility or miscibility of substances because it provides specific interaction information of substances compared to the other solubility parameters.

Using HSPiP, a target substance such as a polymer A, and a single solvent B, which are similar and dissolve well in each other, are calculated in HSP similarity. In order to determine solubility similarity of two substances based on HSP calculation results, whether three elements ($\delta$D, $\delta$P, $\delta$H) of HSP are similar is checked and a $\delta$Tot difference of the two substances is checked.

In an embodiment of the present invention, the following is assumed: under the precondition that a single solvent B for dissolving well a target substance A is provided and a replaceable single solvent is not provided, so long as the amount of the expensive single solvent B may be decreased, price competitiveness may be ensured to thus achieve high profitability. Hence, when a mixed solvent B+C is prepared by adding the single solvent B with an additional solvent C, the amount of the single solvent B is intended to be maximally decreased. Although it is favorable that the amount of the single solvent B of the mixed solvent B+C be smaller, the mixed solvent B+C should have solubility similar to that of the single solvent B and thus the amount of the additional solvent C cannot be continuously increased.

Hence, the additional solvent may be contained in an amount of 0~60 wt %, based on the total weight of the mixed solvent. The solubility similarity of three kinds of substances as above may be evaluated via HSP comparison.

In b), HSP-Diff between HSP of the mixed solvent calculated in a) and HSP of the target substance to be dissolved in the single solvent is calculated.

A difference in the elements of HSP may be determined by calculating HSP-Diff corresponding to vector difference. As the HSP-Diff value of two substances is close to zero, individual substances have similar components responsible for interaction, thus attaining similar HSP (solubility characteristics), which means that such substances dissolve well in each other. As such, HSP-Diff(A,B+C) between the target substance A to be dissolved and the mixed solvent B+C is calculated by Equation 1 below.

$$HSP\text{-}Diff(A,B+C)=(\alpha_1 x |\delta D(A)-\delta D(B+C)|^\beta + \alpha_2 x |\delta P(A)-\delta P(B+C)|^\beta + \alpha_3 x |\delta H(A)-\delta H(B+C)|^\beta)^\gamma \quad \text{[Equation 1]}$$

In Equation 1, A is a target substance to be dissolved; B+C is a mixed solvent comprising a single solvent and an additional solvent; $\alpha_1$, $\alpha_2$, and $\alpha_3$ are real numbers greater than zero and are not particularly limited, but $\alpha_1$ is a real number of 0.5~4.5, $\alpha_2$ is a real number of 0.5~3, and $\alpha_3$ is a real number of 0.5~2.5; $\beta$ is a real number greater than zero and is not particularly limited, but is a real number of 1.0~2.5; and $\gamma$ is a real number excluding zero and is not particularly limited, but is a real number of $-2.5$~$-0.1$ or 0.1~2.5. In the present invention, the values used to calculate HSP-Diff(A,B+C) are $\alpha_1$=1.0, $\alpha_2$=1.0, $\alpha_3$=1.0, $\beta$=2.0, and $\gamma$=0.5.

In the present invention, HSP-Diff depending on an increase in wt % of the additional solvent of the mixed solvent is formed in a two-dimensional graph.

Specifically, the graph in c) represents the x-axis for the amount of the additional solvent, and the y-axis for HSP-Diff calculated in b).

Figure 4:
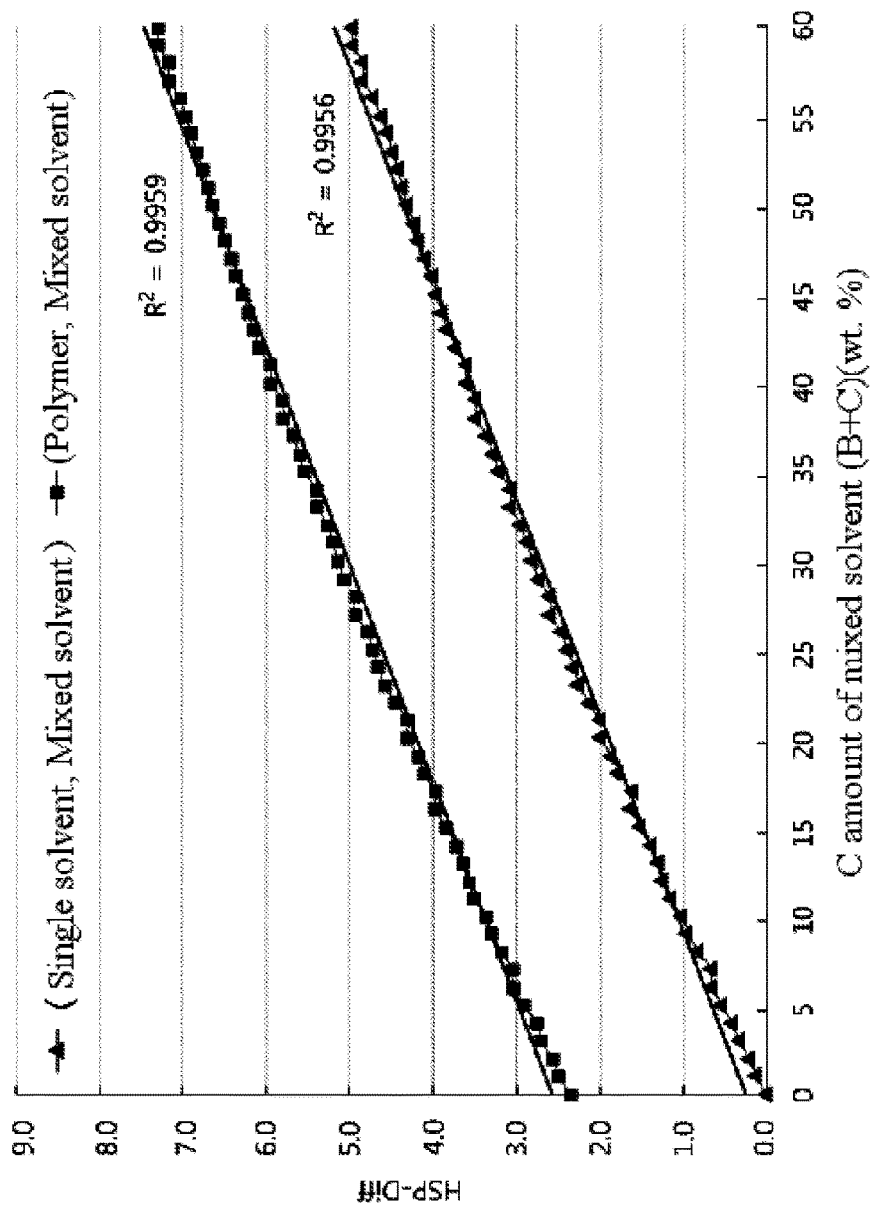
FIG. 4 is a graph illustrating changes in solubility similarity of the mixed solvent B+C, as calculated using HSP-Diff, depending on the amount of the additional solvent C in Example 1 according to the present invention.

In order to compare changes in solubility similarity of the mixed solvent B+C depending on the amount of the additional solvent C according to an embodiment of the present invention, (1) HSP-Diff(single solvent,mixed solvent) between the single solvent B and the mixed solvent B+C, and (2) HSP-Diff(polymer,mixed solvent) between the polymer A and the mixed solvent B+C are calculated and graphed in FIG. 4.

HSP-Diff of the mixed solvent B+C and the single solvent B (polymer A) is linearly increased with an increase in the amount of the additional solvent C, and R-square ($R^2$) corresponding to the coefficient of determinant over the entire range is calculated to be 0.9956 (0.9959). Due to a linear correlation between HSP-Diff of the mixed solvent B+C and the amount of the additional solvent C, the solubility of the mixed solvent B+C sensitively varies depending on an increase in the amount of the additional solvent C, and thus the difference in solubility similarity between the mixed solvent and the polymer A becomes large. Hence, in order to use the mixed solvent B+C in lieu of the single solvent B, the amount of the additional solvent C is determined to be very small (<5 wt %).

The present invention includes d) determining MAX of wt % of the additional solvent such that HSP-Diff depending on the increase in wt % of the additional solvent of the mixed solvent is uniformly maintained within a deviation of 20% or less relative to HSP-Diff at 0 wt % of the additional solvent in the graph formed in c).

Specifically, in d), wt % of the additional solvent such that HSP-Diff is uniformly maintained within a deviation of 20% or less relative to HSP-Diff at 0 wt % of the additional solvent is set to the range of greater than zero but MAX or less (0<additional solvent≤MAX). Thus, when MAX is greater than zero, MAX may be determined to be the maximum amount of the additional solvent. Furthermore, in order to ensure price saving effects, MAX of wt % of the additional solvent such that HSP-Diff is uniformly maintained within a deviation of 20% or less relative to HSP-Diff at 0 wt % of the additional solvent is preferably at least 10 wt %.

In addition, the present invention addresses a system for estimating a mixed solvent for minimizing the amount of a single solvent by the estimation method as above.

The system for estimating a mixed solvent for minimizing the amount of a single solvent comprises:

a first data input module for receiving data for HSP of a mixed solvent prepared by adding a single solvent with an additional solvent depending on an increase in wt % of the additional solvent of the mixed solvent;

a second data input module for receiving data for HSP-Diff between HSP of the mixed solvent input to the first data input module and HSP of a target substance to be dissolved in the single solvent;

a graph determination module for forming a two-dimensional graph of HSP-Diff depending on an increase in wt % of the additional solvent of the mixed solvent; and a maximum value determination module for calculating a maximum value of wt % of the additional solvent such that HSP-Diff depending on the increase in wt % of the additional solvent of the mixed solvent is uniformly maintained within a deviation of 20% or less relative to HSP-Diff at 0 wt % of the additional solvent in the graph formed in the graph determination module.

HSP of the first data input module is represented by HSP=($\delta$D, $\delta$P, $\delta$H) and $\delta$Tot as defined in the aforementioned method.

The amount of the additional solvent may be set to 0~60 wt % based on the total weight of the mixed solvent.

Also, HSP-Diff of the second data input module may be calculated using Equation 1 below.

$$\text{HSP-Diff}(A,B+C)=(\alpha 1 x|\delta D(A)-\delta D(B+C)|^\beta+\alpha 2 x|\delta P(A)-\delta P(B+C)|^\beta+\alpha 3 x|\delta H(A)-\delta H(B+C)|^\beta)^\gamma \quad [\text{Equation 1}]$$

In Equation 1, A is a target substance to be dissolved; B+C is a mixed solvent comprising a single solvent and an additional solvent; $\alpha_1$, $\alpha_2$, and $\alpha_3$ are real numbers greater than zero and are not particularly limited, but $\alpha_1$ is a real number of 0.5~4.5, $\alpha_2$, is a real number of 0.5~3, and $\alpha_3$ is a real number of 0.5~2.5; $\beta$ is a real number greater than zero and is not particularly limited, but is a real number of 1.0~2.5; and $\gamma$ is a real number excluding zero and is not particularly limited, but is a real number of $-2.5$~$-0.1$ or 0.1~2.5. In the present invention, the values used to calculate HSP-Diff(A,B+C) are $\alpha_1$=1.0, $\alpha_2$=1.0, $\alpha_3$=1.0, $\beta$=2.0, and $\gamma$=0.5.

Also, the graph formed in the graph determination module shows the x-axis for the amount of the additional solvent and the y-axis for HSP-Diff calculated in the second data input module.

Also, in the maximum value determination module, wt % of the additional solvent such that HSP-Diff is uniformly maintained within a deviation of 20% or less relative to HSP-Diff at 0 wt % of the additional solvent is set to the range of greater than zero but MAX or less (0<additional solvent≤MAX). Thus, when MAX is greater than zero, MAX may be determined to be the maximum amount of the additional solvent. Furthermore, for price saving effects, MAX of wt % of the additional solvent such that HSP-Diff is uniformly maintained within a deviation of 20% or less relative to HSP-Diff at 0 wt % of the additional solvent is preferably at least 10 wt %.

As used herein, the term "module" refers to one unit for processing a specific function or operation, and may be embodied by hardware, software, or a combination of hardware and software.

MODE FOR INVENTION

A better understanding of the present invention may be obtained via the following examples that are set forth to illustrate, but are not to be construed as limiting the scope of the present invention. The scope of the present invention is described in the claims, and includes all modifications within ranges and meanings equivalent to the claims.

Example 1: Calculation of Changes in Solubility Similarity of Target Substance A, Single Solvent B, Additional Solvent C and Mixed Solvent B+C The following was assumed: under the precondition that a single solvent B for dissolving a polymer A is provided and a replaceable single solvent is not provided, so long as the amount of the expensive single solvent B may be reduced, price competitiveness may be ensured to thus achieve high profitability. To this end, the amount of a single solvent B is intended to be maximally reduced when a mixed solvent B+C is prepared by adding the single solvent B with an additional solvent C. Although it is favorable that the amount of the single solvent B of the mixed solvent B+C is smaller, the mixed solvent B+C should have solubility similar to that of the single solvent B, and thus the amount of the additional solvent C cannot be continuously increased. The solubility similarity of substances may be determined via HSP comparison. Table 1 below shows HSP values of the polymer A, single solvent B, and additional solvent C.

TABLE 1

| Substance | Hansen Solubility Parameter (J/cm$^3$)$^{1/2}$ | | | |
| --- | --- | --- | --- | --- |
| | $\delta$D | $\delta$P | $\delta$H | $\delta$Tot |
| Polymer A | 17.1 | 8.1 | 1.3 | 19.0 |
| Single solvent B | 17.5 | 9.8 | 3.0 | 20.3 |
| Additional solvent C | 17.2 | 14.7 | 9.0 | 24.4 |

In Table 1, the polymer A is polytetrafluoroethylene (CAS number: 9002-84-0), the single solvent B is 4-ethyl-1,3-dioxolan-2-one (CAS number: 4437-85-8), and the additional solvent C is ethyl-isothiocyanate (CAS number: 542-85-8). As such, CAS number stands for Chemical Abstracts Service number, and is a unique identification number of substance.

First, the polymer A and the single solvent B, which are similar and dissolve well in each other, were calculated for HSP similarity. To determine solubility similarity based on HSP values of two substances, whether three elements ($\delta$D, $\delta$P, $\delta$H) of HSP are similar should be checked, and a $\delta$Tot difference of two substances should be checked. A difference in the elements of HSP may be determined by calculating HSP-Diff corresponding to vector difference. As HSP-Diff of two substances is close to zero, individual substances have similar components responsible for interaction, thus attaining similar HSP (solubility characteristics), which means that such substances dissolve well in each other. As such, HSP-Diff(A,B) between the polymer A and the single solvent B was calculated by Equation 1 below.

$$\text{HSP-Diff}(A,B+C) = (\alpha_1 x |\delta D(A) - \delta D(B+C)|^\beta + \alpha_2 x |\delta P(A) - \delta P(B+C)|^\beta + \alpha_3 x |\delta H(A) - \delta H(B+C)|^\beta)^\gamma$$ [Equation 1]

The values used to calculate HSP-Diff(A,B) are $\alpha_1=1.0$, $\alpha_2=1.0$, $\alpha_3=1.0$, $\beta=2.0$, and $\gamma=0.5$.

The polymer A and the single solvent B had an HSP-Diff (A,B) of 2.4 $(J/cm^3)^{1/2}$, and thus were regarded as similar. Also, the δTot difference of the two substances was very small to the level of |19.0−20.3|=1.3 $(J/cm^3)^{1/2}$. The polymer A and the single solvent B were confirmed to dissolve well in each other via HSP similarity comparison.

Figure 3:
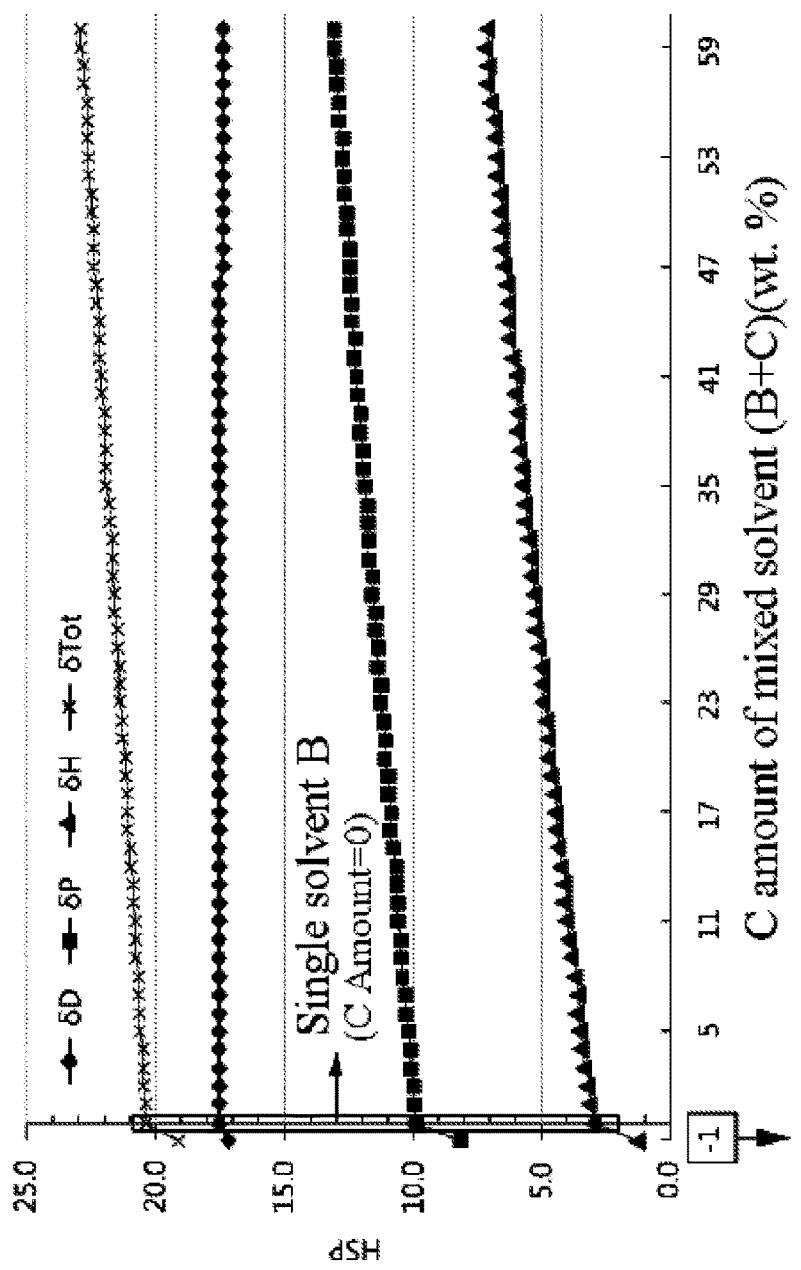
FIG. 3 is a graph illustrating changes in HSP element values of a mixed solvent B+C prepared by adding a single solvent B with an additional solvent C depending on the amount of the additional solvent in Example 1 according to the present invention.

FIG. 3 is a graph illustrating changes in element values of HSP of the mixed solvent B+C prepared by adding the single solvent B with the additional solvent C depending on the amount of the additional solvent C. In order to compare the polymer A with changes in HSP of the mixed solvent depending on the amount of the additional solvent C, the element values of HSP of the polymer A are separately shown as '−1' on the x-axis. The element values of HSP of the single solvent B correspond to the case where the amount of the additional solvent C of the mixed solvent is 0.0.

The δP and δH values of HSP of the mixed solvent B+C are increased in proportion to an increase in the amount of the additional solvent C of the mixed solvent B+C, so that the solubility of the mixed solvent becomes significantly different from that of the single solvent B and the polymer A. The δD value of the mixed solvent B+C was almost constant regardless of the amount of the additional solvent C. Accordingly, an increase in the amount of the additional solvent C resulted in elevated δP and δH of the mixed solvent B+C, and thereby δTot of the mixed solvent B+C became significantly different from that of the single solvent B and the polymer A. Consequently, the solubility of the mixed solvent B+C was increasingly different from that of the polymer A and the single solvent B in proportion to an increase in the amount of the additional solvent C, and thus the mixed solvent B+C was not appropriate as an alternative to decreasing the amount of the single solvent B as typically expected.

FIG. 4 is a graph illustrating (1) HSP-Diff(single solvent, mixed solvent) between the single solvent B and the mixed solvent B+C, and (2) HSP-Diff(polymer,mixed solvent) between the polymer A and the mixed solvent B+C, in order to evaluate changes in solubility similarity of the mixed solvent B+C depending on the amount of the additional solvent C.

HSP-Diff of the mixed solvent B+C and the single solvent B (polymer A) was linearly increased with an increase in the amount of the additional solvent C, and R-square ($R^2$) corresponding to the coefficient of determinant over the entire range was calculated to be 0.9956 (0.9959). Due to a linear correlation between HSP-Diff of the mixed solvent B+C and the amount of the additional solvent C, the solubility of the mixed solvent B+C sensitively varied depending on the amount of the additional solvent C, and thus the difference in solubility similarity between the mixed solvent B+C and the polymer A became significant. Accordingly, the amount of the additional solvent C was determined to be very small (<5 wt %) in order to use the mixed solvent B+C in lieu of the single solvent B.

Based on the evaluation results as above, since an original intention to ensure price competitiveness by maximally decreasing the amount of the single solvent B could not be achieved, the use of the mixed solvent B+C could not decrease the amount of the single solvent B.

Example 2: Calculation of Changes in Solubility Similarity of Target Substance A, Single Solvent B, Additional Solvent D and Mixed Solvent B+D In order to use a mixed solvent obtained by adding a single solvent with an additional solvent as a solution for reducing the amount of a single solvent, the solubility of the mixed solvent should not be significantly changed even when the amount of the additional solvent is increased.

To determine that a mixed solvent is usable, a mixed solvent B+D was made by mixing a single solvent B with an additional solvent D having solubility different from that of the additional solvent C of Example 1, and changes in solubility thereof were calculated compared to the polymer A and the single solvent B. The results are shown in Table 2 below.

TABLE 2

| Substance | Hansen Solubility Parameter $(J/cm^3)^{1/2}$ | | | |
| --- | --- | --- | --- | --- |
| | δD | δP | δH | δTot |
| Polymer A | 17.1 | 8.1 | 1.3 | 19.0 |
| Single solvent B | 17.5 | 9.8 | 3.0 | 20.3 |
| Additional solvent D | 17.2 | 1.8 | 4.3 | 17.8 |

In Table 2, the polymer A is polytetrafluoroethylene (CAS number: 9002-84-0), the single solvent B is 4-ethyl-1,3-dioxolan-2-one (CAS number: 4437-85-8), and the additional solvent D is limonene (CAS number: 5989-27-5).

Figure 5:
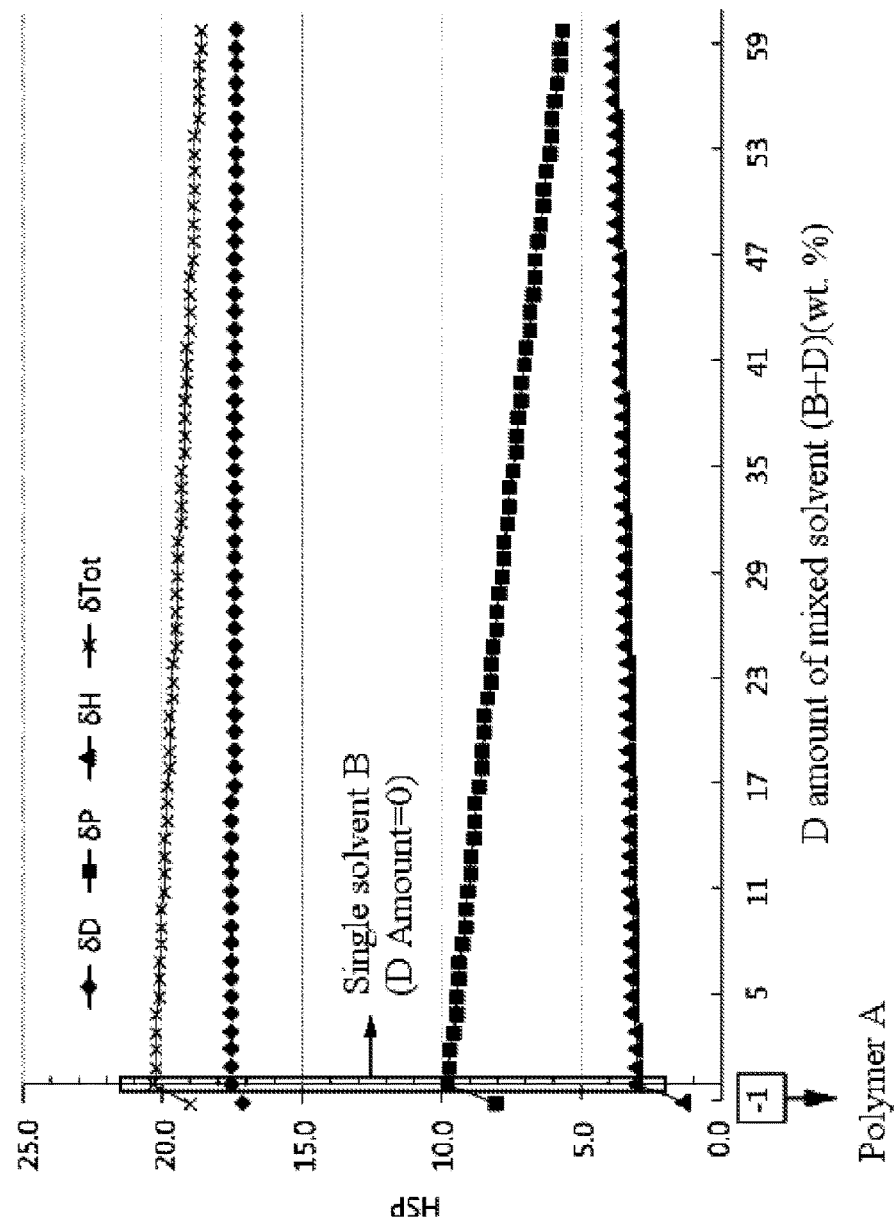
FIG. 5 is a graph illustrating changes in HSP element values of a mixed solvent B+D depending on the amount of an additional solvent D in Example 2 according to the present invention.

FIG. 5 is a graph illustrating changes in the element values of HSP of the mixed solvent B+D depending on the amount of the additional solvent D. Compared to the single solvent B (additional solvent D=0 wt % in the graph), the mixed solvent B+D was increased in a difference in solubility similarity in proportion to an increase in the amount of the additional solvent D. However, the extent of increasing the difference in solubility similarity was different per HSP element. Specifically, as the amount of the additional solvent D was larger, the mixed solvent B+D was remarkably decreased in (1) δP and increased in (2) δH, thus obtaining a significant solubility difference from the single solvent B. Thus, δTot of the mixed solvent B+D was gradually decreased due to such effects, and thereby the difference in solubility similarity between the mixed solvent and the single solvent B became slightly large.

When comparing changes in solubility similarity between the polymer A and the mixed solvent B+D, δP of the mixed solvent B+D was decreased in proportion to an increase in the amount of the additional solvent D, and ultimately became closer to δP of the polymer A to be dissolved, rather than the single solvent B. Briefly, δP of the mixed solvent B+D was decreased and thus became more different from that of the single solvent B but was less different from that of the polymer A. The δP difference between the mixed solvent B+D and the polymer A was continuously decreased until the amount of the additional solvent D was 27 wt %, and then increased again. Therefore, the solubility of the mixed solvent was always significantly different from that of the single solvent, but could be rather close to the polymer to be dissolved.

Figure 7:
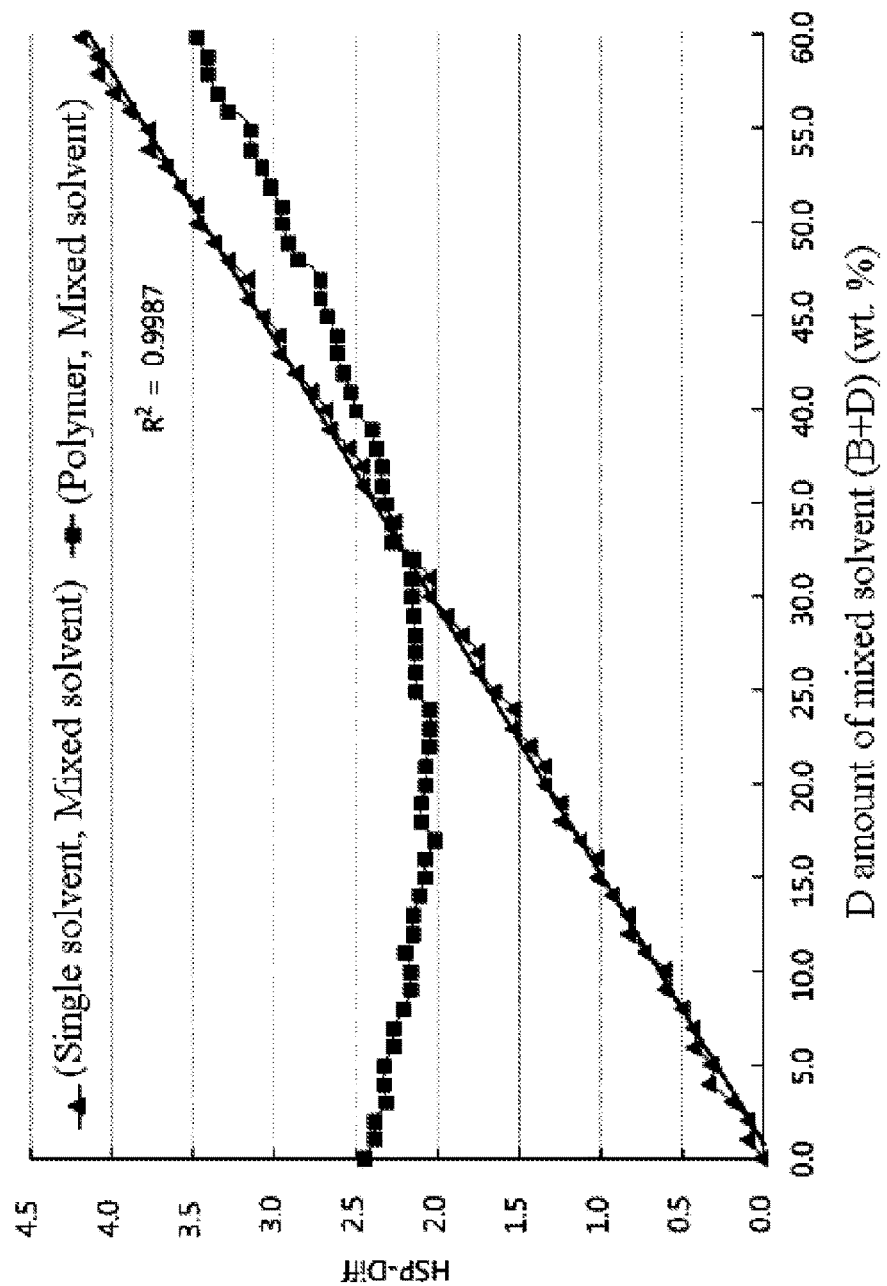
FIG. 7 is a graph illustrating HSP-Diff of the mixed solvent B+D calculated for a polymer A (polymer, mixed solvent) and a single solvent B (single solvent, mixed solvent) to evaluate changes in solubility of the mixed solvent B+D in Example 2 according to the present invention.
Figure 8:
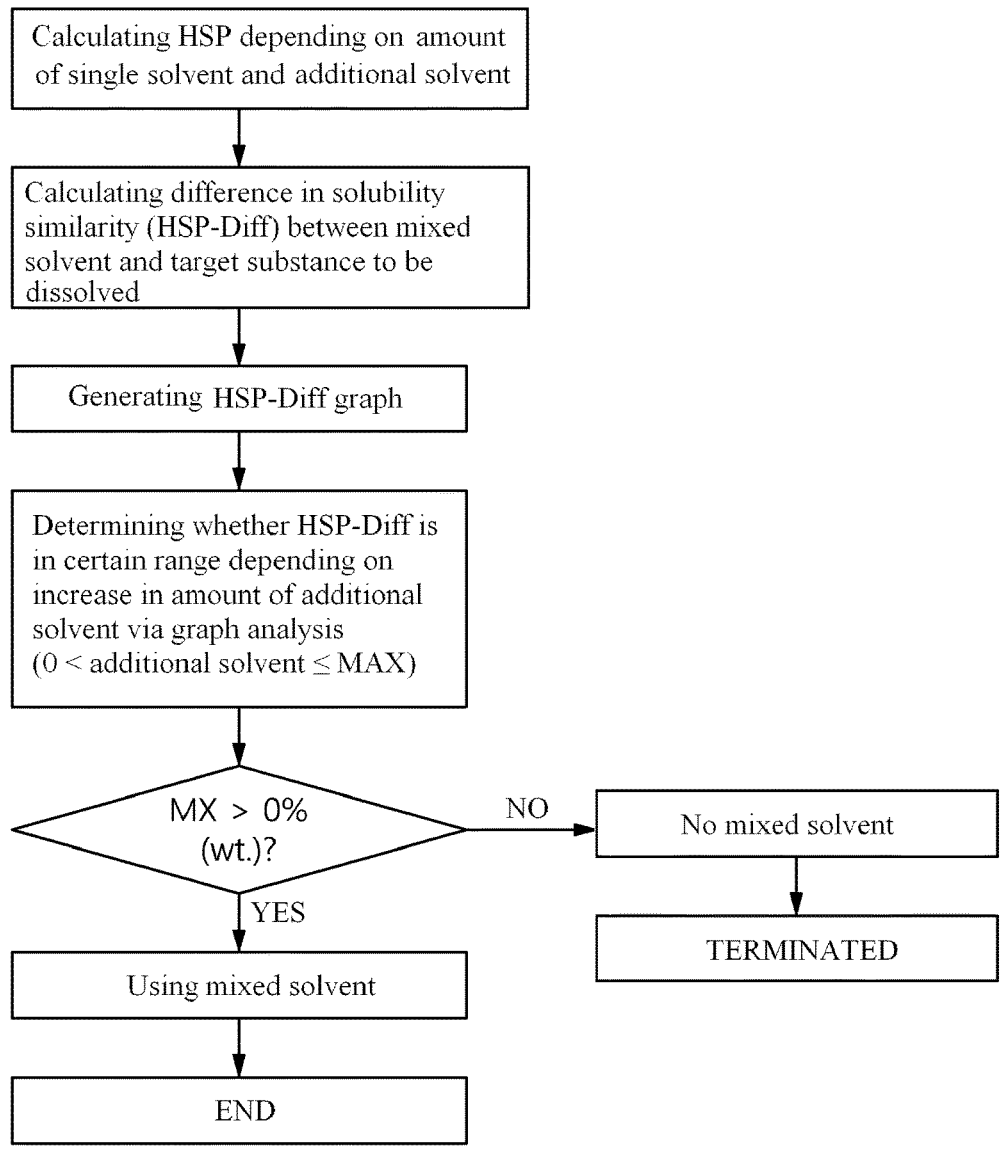
FIG. 8 is a flowchart illustrating G-MRDSE according to the present invention.

FIG. 7 is a graph illustrating HSP-Diff of the mixed solvent for the polymer A (polymer, mixed solvent) and single solvent B (single solvent, mixed solvent) to evaluate changes in solubility of the mixed solvent B+D. The changes in HSP-Diff between the mixed solvent B+D and the polymer A may be largely divided into two zones. Specifically, HSP-Diff is slightly decreased or becomes constant until the amount of the additional solvent reaches a predetermined value from 0 wt %, and then is increased in proportion to the amount of the additional solvent. The reason why HSP-Diff of the mixed solvent B+D for the polymer A is substantially maintained constant is that a decrease in δP difference between the polymer and the mixed solvent is offset with an increase in δH difference therebetween as mentioned above. The HSP-Diff is maintained constant, and then both δP and δH differences are increased when the additional solvent is contained in a predetermined amount or more, ultimately increasing HSP-Diff. The largest amount of the additional solvent that enables HSP-Diff to be maintained constant is a maximum value (MAX). On the graph, MAX of the additional solvent D is about 40 wt %. When the mixed solvent B+D having a composition of B:D=60:40 (wt %) is used, it may be used to dissolve the polymer A, instead of the single solvent B, and thus the amount of the single solvent B may be reduced by 40% in maximum. δTot of the mixed solvent B+D at MAX was 19.1, which is very similar to 19.0 of the polymer A.

Depending on the solubility characteristics of the additional solvent, the mixed solvent obtained in such a manner that the additional solvent is added to the single solvent may be used to decrease the amount of the single solvent. Furthermore, the maximum composition of the mixed solvent may be determined via calculation of HSP-Diff between the mixed solvent and the polymer to be dissolved, making it possible to minimize the amount of the single solvent.

Therefore, the mixed solvent obtained by adding the single solvent with the additional solvent can be used to decrease the amount of the single solvent. Also, the use of the mixed solvent can be determined depending on the solubility of the additional solvent. Thereby, the maximum amount of the additional solvent of the mixed solvent can be finally calculated via graph analysis.

The invention claimed is:

1. A method of producing a mixed solvent for minimizing an amount of a single solvent, wherein in a target substance to be dissolved, a single solvent for dissolving the target substance, and a mixed solvent comprising the single solvent and an additional solvent, the mixed solvent that is used to dissolve the target substance contains the single solvent in a minimum amount, the method comprising:
   a) calculating, by a first module, a Hansen solubility parameter (HSP) of a mixed solvent prepared by adding a single solvent with an additional solvent depending on an increase in wt % of the additional solvent of the mixed solvent;
   b) calculating, by a second module, an HSP difference (HSP-Diff) between HSP of the mixed solvent calculated in a) and HSP of a target substance to be dissolved in the single solvent;
   c) forming, by a graph determining module, a two-dimensional graph of HSP-Diff depending on an increase in wt % of the additional solvent of the mixed solvent; and
   d) determining, by a maximum value determination module, a maximum value (MAX) of wt % of the additional solvent such that HSP-Diff depending on the increase in wt % of the additional solvent of the mixed solvent is uniformly maintained within a deviation of 20% or less relative to HSP-Diff at 0 wt % of the additional amount in the graph formed in c); and
   e) mixing the single solvent with the additional solvent in an amount equal to or less than the maximum value (MAX) of wt % of the additional solvent to produce the mixed solvent.

2. The method of claim 1, wherein the HSP in a) is HSP=(δD, δP, δH) and δTot, wherein δD is a nonpolar solubility parameter owing to dispersion interactions, δP is a polar solubility parameter owing to permanent dipole-permanent dipole interactions, δH is a hydrogen bond solubility parameter, and δTot is a magnitude of the HSP vector.

3. The method of claim 1, wherein the additional solvent is contained in an amount of 0~60 wt % based on a total weight of the mixed solvent.

4. The method of claim 1, wherein the HSP-Diff in b) is calculated using Equation 1 below:

$$\text{HSP-Diff}(A,B+C) = (\alpha_1 x |\delta D(A) - \delta D(B+C)|^\beta + \alpha_2 x |\delta P(A) - \delta P(B+C)|^\beta + \alpha_3 x |\delta H(A) - \delta H(B+C)|^\beta)^\gamma \quad \text{[Equation 1]}$$

wherein A is a target substance to be dissolved, B+C is a mixed solvent comprising a single solvent and an additional solvent, $\alpha_1$, $\alpha_2$, and $\alpha_3$ are real numbers greater than zero, β is a real number greater than zero, and γ is a real number excluding zero.

5. The method of claim 4, wherein $\alpha_1$ is a real number of 0.5~4.5, $\alpha_2$ is a real number of 0.5~3, $\alpha_3$ is a real number of 0.5~2.5, β is a real number of 1.0~2.5, and γ is a real number of −2.5~−0.1 or 0.1~2.5.

6. The method of claim 1, wherein the graph in c) shows an x-axis for an amount of the additional solvent and a y-axis for HSP-Diff calculated in b).

7. The method of claim 1, wherein in d), the MAX of wt % of the additional solvent such that HSP-Diff is uniformly maintained within a deviation of 20% or less relative to HSP-Diff at 0 wt % of the additional amount is 10 wt % or more.

* * * * *